«12» United States Patent
Huxley et al.

US011203628B2

(10) Patent No.: US 11,203,628 B2
(45) Date of Patent: Dec. 21, 2021

(54) CD200 MUTANTS AND ITS USES

(71) Applicant: Ducentis Biotherapeutics Ltd., Oxfordshire (GB)

(72) Inventors: Philip Huxley, Oxfordshire (GB); Joseph Sheridan, Oxfordshire (GB); Jonathan Heal, Oxfordshire (GB)

(73) Assignee: Ducentis Biotherapeutics Ltd., Witney Oxfordshire (GB)

( * ) Notice: Subject to any disclaimer, the term of this patent is extended or adjusted under 35 U.S.C. 154(b) by 430 days.

(21) Appl. No.: 16/300,382

(22) PCT Filed: May 10, 2017

(86) PCT No.: PCT/GB2017/051303
§ 371 (c)(1),
(2) Date: Nov. 9, 2018

(87) PCT Pub. No.: WO2017/194941
PCT Pub. Date: Nov. 16, 2017

(65) Prior Publication Data
US 2019/0367580 A1 Dec. 5, 2019

(30) Foreign Application Priority Data
May 10, 2016 (GB) .................................. 1608197

(51) Int. Cl.
*C07K 14/705* (2006.01)
*A61K 38/17* (2006.01)
*C07K 16/28* (2006.01)
*C12N 15/62* (2006.01)

(52) U.S. Cl.
CPC .... *C07K 14/70503* (2013.01); *A61K 38/1774* (2013.01); *C07K 16/2803* (2013.01); *C07K 2319/30* (2013.01); *C12N 15/62* (2013.01)

(58) Field of Classification Search
None
See application file for complete search history.

(56) References Cited
U.S. PATENT DOCUMENTS
2005/0048069 A1  3/2005  Gorczynski et al.

FOREIGN PATENT DOCUMENTS
WO   WO 2001/066689 A2   9/2001
WO   WO 2002/042332 A2   5/2002
WO   WO 2017/194941 A1   11/2017

OTHER PUBLICATIONS

Li et al. 'Aberrant CD200/CD200R1 expression and function in systemic lupus erythematosus contributes to abnormal T-cell responsiveness and dendritic cell activity.' Arth. Res. Ther. 14(3):R123, 2012.*
Database Genseq [Online], "Novel human secretory protein, Seq. ID No. 672", retrieved from EBI Accession No. GSP:AAU28315, 2 pgs., Dec. 18, 2001.
Hatherley et al., "Recombinant CD200 protein does not bind activating proteins closely related to CD200 receptor", J. Immunol., vol. 175, No. 4, pp. 2469-2474 (2005).
Hatherley et al., "Structures of CD200/CD200 receptor family and implications for topology, regulation, and evolution", Structure, vol. 21, No. 5, pp. 820-832 (2013).
Holmannova et al., "CD200/CD200R Paired Potent Inhibitory Molecules Regulating Immune and Inflammatory Responses; Part I: CD200/CD200R Structure, Activation, and Function", Acta Medica, vol. 55, pp. 12-17 (2012).
International Search Report from International Patent Application No. PCT/GB2017/051303, 11 pages, dated Jul. 3, 2017, Application now published as International Publication No. WO2017/194941 on Nov. 16, 2017.
Jiang et al., "CD200Fc reduces TLR4-mediated inflammatory responses in LPS-induced rat primary microglial cells via inhibition of the NF-κB pathway", Inflammation Research, vol. 65, pp. 521-532 (2016).
Wright et al., "Characterization of the CD200 receptor family in mice and humans and their interactions with CD200", J. Immunol., vol. 171, No. 6, pp. 3034-3046 (2003).

* cited by examiner

*Primary Examiner* — Nora M Rooney
(74) *Attorney, Agent, or Firm* — McDermott Will & Emery LLP; Judy M. Mohr; Brett A. Schweers

(57) ABSTRACT

The invention relates generally to mutant CD200 proteins which bind with greater affinity to the CD200 receptor than wild-type CD200, in particular the invention relates to a mutated CD200 protein comprising a mutation at amino acid residue position 130 and/or 131. This invention also relates to a fusion protein comprising the protein as defined herein fused to a non-CD200 protein encoding portion via an optional linker portion, a pharmaceutical composition comprising the protein as defined herein and uses thereof.

19 Claims, 6 Drawing Sheets

Specification includes a Sequence Listing.

A: Size Exclusion Chromatograph of K130Y

B: Size Exclusion Chromatograph of I131Y

A: Sensorgram showing the association and dissociation phases of CD200R binding to captured WT CD200

B: Sensorgram showing the association and dissociation phases of CD200R binding to captured K130Y

CD200 MUTANTS AND ITS USES

CROSS-REFERENCE TO RELATED APPLICATIONS

This application is a U.S. National Phase under 35 U.S.C. § 371 of International Application No. PCT/GB2017/051303, with an International Filing Date of May 10, 2017, which claims priority under to GB Patent Application No. 1608197.8 filed on May 10, 2016, each of which is hereby incorporated by reference in its entirety.

REFERENCE TO SEQUENCE LISTING

A sequence listing was submitted electronically via EFS in the form of a text file on Nov. 9, 2018, and named "U.S. Ser. No. 16/300,382.txt" (36.98 kilobytes). A replacement sequence listing is being submitted electronically via EFS in the form of a text file, created Mar. 29, 2019, and named "Replacement_Sequence_Listing.txt" (37.86 kilobytes), the contents of which are incorporated herein by reference in their entirety.

FIELD OF THE INVENTION

The invention relates generally to mutant CD200 proteins which bind with greater affinity to the CD200 receptor than wild-type CD200, in particular the invention relates to a mutated CD200 protein comprising a mutation at amino acid residue position 130 and/or 131. This invention also relates to a fusion protein comprising the protein as defined herein fused to a non-CD200 protein encoding portion via an optional linker portion, a pharmaceutical composition comprising the protein as defined herein and uses thereof.

BACKGROUND OF THE INVENTION

Autoimmune diseases are the second leading cause of chronic illness globally and in the U.S they are the leading cause of morbidity in women. According to a 2008 international survey, chronically ill patients in the U.S. as compared with those in other countries are more likely to do without proper care due to the burden of cost (Schoen, C. et al., (2008) *Health Affairs Web Exclusive*, w1-w16). Additionally, these patients are more likely to experience the highest rates of medical errors, problems with coordination of care, and high out-of-pocket health care costs.

Currently, the American Autoimmune Related Disease Association (AARDA) estimates that 50 million Americans have an autoimmune disease. Epidemiological data are lacking to determine the full direct and indirect cost to the overall health care system due to autoimmune disease. However, in 2001, the National Institutes of Allergy and Infectious Diseases (NIAID) Director Dr. Anthony Fauci estimated that annual autoimmune disease treatment costs were greater than $100 billion. While $100 billion is a staggering figure, it is likely a vast understatement of the true costs of autoimmune disease as the annual costs of only seven of the 100+ known autoimmune diseases, Crohn's disease, ulcerative colitis, systemic lupus erythematosus (SLE), multiple sclerosis (MS), rheumatoid arthritis (RA), psoriasis, and scleroderma, are estimated through epidemiological studies to total from $51.8-$70.6 billion annually. Furthermore, these estimates overlook the cost of immunosuppressive therapy during transplantation.

Autoimmune diseases are chronic conditions with no cure, which arise when the immune system decides that healthy cells are foreign and attacks them. Depending on the type, an autoimmune disease can affect one or many different types of body tissue and can cause abnormal organ growth and changes in organ function. The normal regulation of the immune system is largely due to receptor/ligand pairs that includes proteins that are expressed by cells involved in an immune response. However, these receptor/ligand pairs are often included in signaling cascades which provides a hurdle for the treatment of autoimmune diseases. The current management of autoimmune diseases involves attempts to control the process of the disease and to decrease the symptoms, especially during flare-ups.

OX-2 membrane glycoprotein, also named CD200 (Cluster of Differentiation 200), is a human protein encoded by the CD200 gene which is expressed in a variety of cell types (Barclay, A. N. (1981) Immunology 44, 727) and has a high degree of homology to molecules of the immunoglobulin gene family. The protein encoded by this gene is a type-1 membrane glycoprotein which contains two immunoglobulin domains and binds to the CD200 receptor (CD200R).

CD200R is expressed on myeloid cells (monocytes, macrophages, dendritic cells and eosinophils) and T cells (Wright, et al., (2000), *Immunity* 12, 233-242; Wright, et al., (2003), *J. Immunol,* 171, 3034-3046).

Engagement of CD200 with CD200R delivers an inhibitory signal to myeloid and T-cells, thus exerting an immunosuppressive effect on both the innate and adaptive arms of the immune system (Rahim S. A., (2005) AIDS, 19, 1907-1925; Shiratori, I., (2005) *J. Immunol,* 175, 4441-4449; Misstear, K., et al., (2012), *Journal of Virology,* 86(11), 6246-6257).

CD200R agonists have been shown to reduce pathology in a wide range of disease models, for example arthritis (Gorczynski, et al., (2001) *Clin. Immunol.* 101, 328-34; Gorczynski, et al., (2002) *Clin. Immunol.* 104, 256-264), graft rejection (Gorczynski, et al., (2002) *Transplantation* 73, 1948-1953), failed pregnancy (Gorczynski, et al., (2002) *Am. J. Reprod. Immunol.,* 48, 18-26), contact hypersensitivity (Rosenblum, et al., (2004) *Blood* 103, 2691-8), influenza induced lung inflammation (Snelgrove, et al., (2008) *Nat. Immunol.,* 9, 1074-1083) and HSV-induced inflammatory lesions (Sarangi, et al., (2009) *Clin. Immunol.* 131, 31-40).

Additionally, CD200$^{-/-}$ mice challenged with influenza virus developed more severe disease, which was associated with increased lung infiltration and lung endothelium damage, compared with wildtype controls (Rygiel. T. P., et al. (2009) *J. Immunol.* 183(3), 1990-1996). CD200$^{-/-}$ mice did develop immune responses that could control viral load, suggesting that the severe disease was caused by an exaggerated immune response. Disease could be prevented by T-cell depletion before viral challenge, despite the dramatically increased viral load that resulted. Rygiel. T. P., et al. (2009) concluded that T cells are essential for the manifestation of disease symptoms during influenza infection, and that lack of down-modulating CD200-CD200R signalling, rather than viral load, increases immune pathology.

Profiling studies have shown that hCD200 expression is down regulated in diverse patient populations, such as patients with multiple sclerosis (Koning, et al., (2007) *Ann. Neurol.* 62, 504-514), asthma exacerbation (Aoki, et al., (2009) *Clin. Exp. Allergy* 39, 213-221), Alzheimer's disease (Walker, et al., (2009) *Exp. Neurol.* 215, 5-19), primary hypertrophic osteoarthropathy (Ren, et al., (2013) *Rheumatol. Int.* 33(10), 2509-2512), failed pregnancy (Clark (2009)

*Am. J. Reprod. Immunol.* 61, 75-84) and lichen planopilaris (hair loss) (Harries, et al., (2013) *J. Pathol.* 231(2), 236-247).

Agonist CD200 proteins are disclosed in, for example, WO 2000/061171 and WO 2008/089022. The literature describes the use of wild-type CD200 molecules to modulate immune cell function. This invention relates to mutant CD200 proteins which bind with greater affinity to the CD200 receptor than wild-type CD200.

There is therefore a need to provide improved clinical efficacy at lower doses which will overcome the problems associated with currently available treatments to autoimmune diseases.

SUMMARY OF THE INVENTION

According to a first aspect of the invention, there is provided a mutated CD200 protein comprising a mutation at amino acid residue position 130 and/or 131.

According to a second aspect of the invention, there is provided a fusion protein comprising the protein as defined herein fused to a non-CD200 protein encoding portion via an optional linker portion.

According to a third aspect of the invention, there is provided a polynucleotide encoding a protein as defined herein.

According to a further aspect of the invention, there is provided a pharmaceutical composition comprising the protein as defined herein.

According to a further aspect of the invention, there is provided the protein as defined herein or the composition as defined herein for use in the treatment of autoimmune disease.

DETAILED DESCRIPTION OF THE INVENTION

Figure 1:
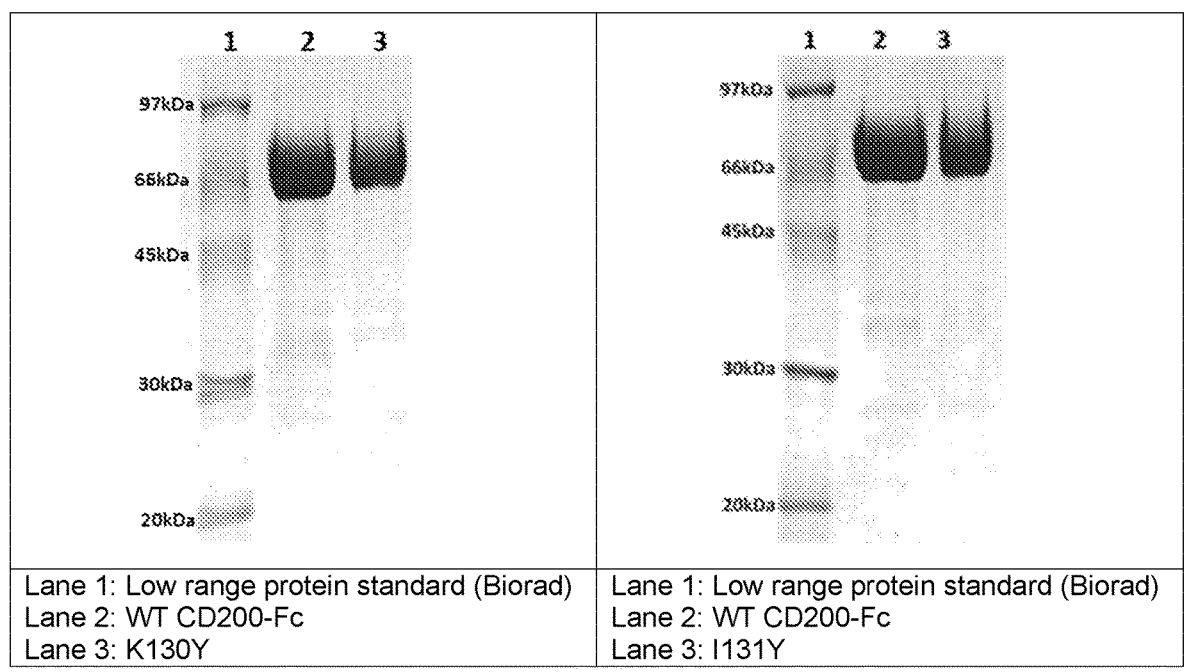
FIG. 1: SDS gels of WT-CD200-Fc, K130Y and I131Y.

According to a first aspect of the invention, there is provided a mutated CD200 protein comprising a mutation at amino acid residue position 130 and/or 131. The inventors have found that mutations in the extracellular domain of CD200 at these particular amino acid residues produces a mutant CD200 with increased binding affinity to the CD200 receptor (CD200R). Additionally, the mutated CD200 proteins as described herein have significant benefits, in particular in respect to providing treatment with greater clinical efficacy and at lower doses.

The term "CD200 protein" as used herein, refers to wild-type CD200 protein.

The term "wild-type" as used herein, refers to proteins, peptides, amino acid and nucleotide sequences which are present in nature. For example, the term "wild-type CD200 protein" as used herein, refers to any full length isoform of CD200 (UNIPROT P41217 OX2G_HUMAN; SEQ ID NO: 1) or any portion thereof, which binds to the CD200 receptor. CD200 protein is also known as OX-2 membrane glycoprotein.

Wild-type CD200 is a cell surface protein, having an N-terminal extracellular domain, and short transmembrane and cytoplasmic domains. The extracellular domain binds to target receptors such as the CD200 receptor. In one embodiment, the CD200 protein is the extracellular domain of CD200, or any portion thereof, which binds to the CD200 receptor. In a further embodiment, the CD200 protein is the extracellular domain (SEQ ID NO: 2) of wild type CD200 which, in the full length protein including the signal sequence, begins with glutamine at position +31 and ends at lysine at position +231 (SEQ ID NO: 1).

The term "position" as used herein, refers to the residue number in an amino acid sequence where 1 is the first translated amino acid.

The term "mutated" or "mutation" as used herein, refers to proteins, peptides, amino acid and nucleotide sequences which have undergone a change in their form from the wild-type equivalent to become a mutant. For example, a mutated or mutant protein may have undergone a change in the amino acid and/or nucleotide sequence when compared to the corresponding wild-type sequence, such a change may also be referred to as a mutation.

Common mutations include substitutions, deletions, additions, truncations, translocation and inversions. Therefore, in one embodiment the mutation is a substitution, translocation or inversion. In a further embodiment, the mutation is a substitution mutation. In a further embodiment, said substitution mutation is K130Y and/or I131Y.

It will be understood by one skilled in the art that a mutation in a nucleotide sequence which does not alter the amino acid sequence will still be considered to be mutated. Consequently, a mutation in a nucleotide sequence which does not alter the protein will still be considered to be mutated.

The term "mutated CD200 protein" as used herein, refers to full length CD200 protein or any portions thereof, which binds to the CD200 receptor, comprising a mutated amino acid residue or multiple mutated amino acid residues in the amino acid sequence so that it is similar but no longer identical to the wild-type CD200 protein.

In one embodiment, the mutated CD200 protein may be made synthetically or recombinantly. In a further embodiment, the mutated CD200 protein may be made synthetically. In an alternative embodiment, the mutated CD200 protein may be made recombinantly.

In one embodiment, the mutated CD200 protein binds to the CD200 receptor with greater affinity than wild-type CD200.

In one embodiment, the mutated CD200 protein may comprise a biologically or chemically active non-CD200 component therein or attached thereto.

In one embodiment, the mutated CD200 protein may be soluble (i.e. circulating) or bound to a surface. In a further embodiment, the mutated CD200 protein is soluble. In an alternative embodiment, the mutated CD200 protein is bound to a surface.

In one embodiment, the mutated CD200 protein may include the entire extracellular domain of CD200 or portions thereof.

The term "portion" as used herein with reference to proteins, peptides and amino acid and nucleotide sequences, refers to fragments and derivatives that are functional, i.e. bind to their target.

The term "fragment" as used herein refers to a part of a protein, peptide, amino acid or nucleotide sequence that recognises and binds its target, such as a receptor.

The term "derivatives of" and "mutant" as used herein, refer to a protein, peptide, amino acid or nucleotide sequence that shares at least 70% (such as 75%, 80%, 85%, 90%, 95% or 99%) sequence similarity with and functions like the wild-type equivalent. Thus, a mutant may be a derivative of a wild-type equivalent. In a further embodiment, the mutated CD200 protein is a portion of the extracellular domain of wild-type CD200 starting with a glutamine at position +31 and ending with a lysine at position +231.

The term "amino acid residue" as used herein, refers to a monomeric unit in a polymeric chain, i.e. a single amino acid in a protein.

In one embodiment, the protein additionally comprises one or more mutations present in the amino acid sequence, for example 1-15 mutations.

In a further embodiment, said mutated protein comprises one or more additional mutations such as those selected from G129I, F128R and/or N81K.

In one embodiment, the protein as defined herein comprises the extracellular domain (ECD) of said protein. In a further embodiment, the protein as defined herein comprises the sequence of SEQ ID NO:3 or SEQ ID NO: 4.

In one embodiment, the protein as defined herein comprises the full length CD200 sequence. In a further embodiment, the protein as defined herein comprises the sequence of SEQ ID NO: 12 or SEQ ID NO: 13.

Figure 5:
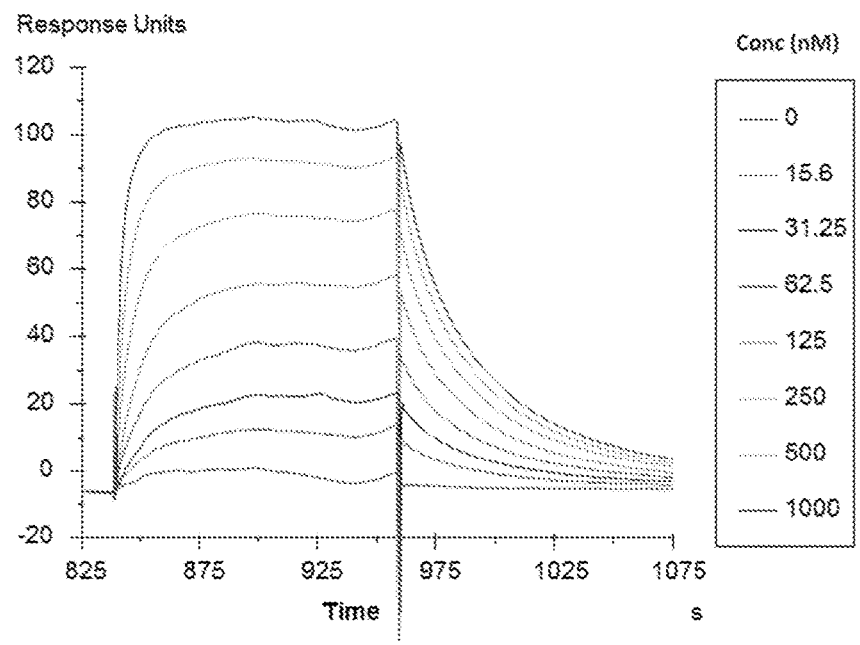
FIG. 5: A: Sensorgram showing the association and dissociation phases of CD200R binding to captured wild-type CD200.
B: Sensorgram showing the association and dissociation phases of CD200R binding to captured K130Y.
Figure 5:
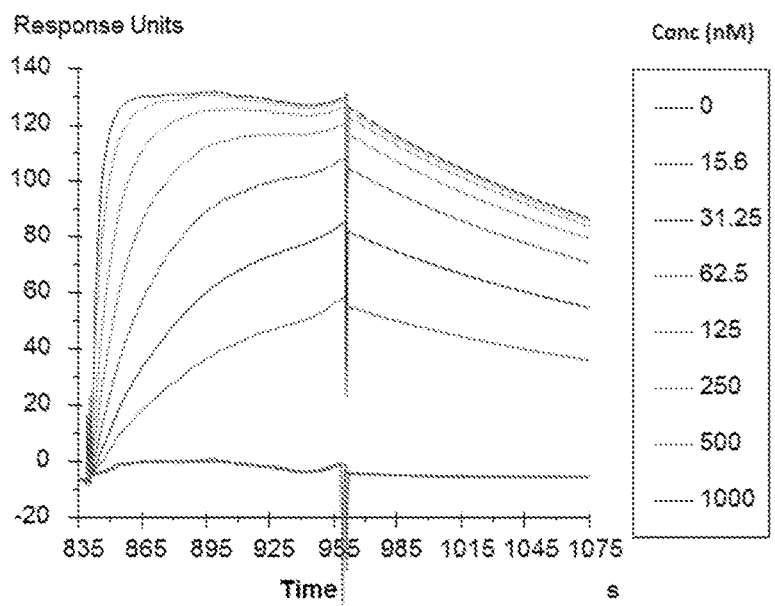

As presented in FIG. 5 and Table 2, the mutated CD200 proteins disclosed herein bind more tightly to the CD200 receptor and exhibit longer residence time on the receptor than wild-type CD200 protein.

Fusion Protein

According to a second aspect of the invention, there is provided a fusion protein comprising the protein as defined herein fused to a non-CD200 protein encoding portion via an optional linker portion.

The term "fusion protein" as used herein, refers to one or more amino acid sequences, peptides and/or proteins joined together using methods well known in the art and as described in, for example U.S. Pat. Nos. 5,434,131 and 5,637,481. The joined amino acid sequences, peptides or proteins thereby form one fusion protein.

In one embodiment, the protein herein is fused at the N- or C-terminus to a non-CD200 protein encoding portion via an optional linker portion. In a further embodiment, the protein herein is fused at the N-terminus to a non-CD200 protein encoding portion via an optional linker portion. In an alternative embodiment, the protein herein is fused at the C-terminus to a non-CD200 protein encoding portion via an optional linker portion In one embodiment, said linker portion is a peptide comprises between 1 and 15 amino acids. In a further embodiment, the linker is a 10 amino acid linker starting with a glycine and ending with a serine. In still a further embodiment, the linker is a peptide comprising the sequence of GGGGSGGGGS (SEQ ID NO: 11).

The term "non-CD200 protein encoding portion" as used herein, refers to any peptide or protein that does not bind to the CD200 receptor and does not interfere with the binding of CD200 to its target. Examples include, but are not limited to, an immunoglobulin (Ig) constant region or portion thereof.

In a further embodiment, said non-CD200 protein encoding portion is an antibody or fragment thereof. In a further embodiment, said non-CD200 protein encoding portion is an Fc fragment. Therefore, the mutated CD200 fusion protein as described herein may also be called a mutant CD200-Fc. In a further embodiment, the Fc fragment is mammalian derived, such as derived from a human or monkey, such as human C(gamma)1 which includes the hinge, CH2 and CH3 regions. The Fc fragment is believed to provide the advantage of increasing the half-life (i.e. receptor occupancy) of the mutated CD200 proteins of the invention. It will be understood by one skilled in the art that the Fc region may be mutated to reduce its effector functions (see for example, U.S. Pat. Nos. 5,637,481 and 6,132,992).

As mutated CD200 proteins have a higher affinity for the CD200 receptor compared to wild type or non-mutated CD200 proteins, as presented herein in FIG. 5 and Table 2, any fused non-CD200 protein encoding portion will also benefit from this feature. This provides substantial benefit for pharmaceutical compositions and therapies, as described herein.

In one embodiment, the fusion protein as defined herein comprises the sequence of SEQ ID NO: 6 or SEQ ID NO: 7.

The proteins of the present invention are preferably produced by recombinant DNA methods by inserting a nucleic acid sequence encoding mutated CD200 protein or any portion thereof into a recombinant expression vector and expressing the nucleic acid sequence in a recombinant expression system under conditions promoting expression. Therefore, in one embodiment, the polynucleotide encoding the fusion protein additionally comprises a vector, such as pcDNA 3.4. In one embodiment, the fusion protein is flanked by one or more restriction enzyme sites, such as Hind III and/or Xho I. In a further embodiment, the polynucleotide encoding the fusion protein is flanked by Hind III and Xho I restriction sites.

In one embodiment, the fusion protein comprises one or more restriction enzyme sites, such as Bam HI.

According to a third aspect of the invention, there is provided a polynucleotide encoding a protein as defined herein. Nucleic acid sequences encoding the proteins provided by this invention can be assembled from cDNA fragments and short oligonucleotide linkers, or from a series of oligonucleotides, to provide a synthetic gene which is capable of being inserted in a recombinant expression vector and expressed in a recombinant transcriptional unit.

Recombinant expression vectors include synthetic or cDNA-derived nucleic acid fragments encoding mutated CD200 operably linked to suitable transcriptional or translational regulatory elements derived from mammalian, microbial, viral or insect genes. Such regulatory elements include a transcriptional promoter, an optional operator sequence to control transcription, a sequence encoding suitable mRNA ribosomal binding sites, and sequences which control the termination of transcription and translation. The ability to replicate in a host, usually conferred by an origin of replication, and a selection gene to facilitate recognition of transformants may additionally be incorporated.

Therapeutic Uses

The invention has particular application in therapy because the interaction between the CD200 protein and the CD200 receptor is characterized by rapid "on" rates and rapid dissociation ("off") rates which in turn decreases the affinity of CD200 for the CD200 receptor. Therefore, increasing the affinity of mutant CD200 protein for the CD200 receptor as presented herein, can be used in the manufacture of pharmaceutical compositions with more potent properties.

Furthermore, manufacturing costs for recombinant proteins are high and the mutant CD200 protein, having higher affinity, can be used in pharmaceutical compositions at significantly lower doses than wild type or non-mutated CD200 protein to achieve a therapeutic effect. Use of the mutant CD200 protein may therefore be more cost effective in addition to being more clinically effective.

According to a further aspect of the invention, there is provided a pharmaceutical composition comprising the protein as defined herein.

In one embodiment, the mutated CD200 protein as defined herein is a modulator of the CD200 receptor. The term "modulator" as used herein, refers to a substance which results in a kinetic change, for example a modulator of a protein may result in an increase or decrease in the activity of said protein. In view of the properties of the mutated CD200 proteins of the invention, they are believed to be agonists of the CD200 receptor and therefore find utility in the treatment of autoimmune disease. Therefore, in a further embodiment, the mutated CD200 protein as defined herein is an agonist of the CD200 receptor.

Thus, according to a further aspect of the invention, there is provided the protein as defined herein or the composition as defined herein for use in the treatment of autoimmune disease.

Fusion proteins comprising the mutant CD200 proteins defined herein may deactivate activated immune cells with higher efficiency than fusion proteins comprising wild-type or non-mutated CD200 proteins.

In one embodiment, the autoimmune disease is selected from autoimmune diseases affecting the neuromuscular system, vascular system, eye, digestive tract, lung, kidney, liver, peripheral or central nervous system, bone, cartilage or joints.

In a further embodiment, the autoimmune disease is one or more autoimmune diseases selected from: acute disseminated encephalomyelitis (ADEM); acute necrotizing haemorrhagic leukoencephalitis; Addison's disease; agammaglobulinemia; alopecia areata; amyloidosis; ankylosing spondylitis; anti-GBM/anti-TBM nephritis; antiphospholipid syndrome (APS); Autoimmune angioedema; autoimmune aplastic anemia; autoimmune dysautonomia; autoimmune hepatitis; autoimmune hyperlipidemia; autoimmune immunodeficiency; autoimmune inner ear disease (AIED); autoimmune myocarditis; autoimmune oophoritis; autoimmune pancreatitis; autoimmune retinopathy; autoimmune thrombocytopenic purpura (ATP); autoimmune thyroid disease; autoimmune urticarial; axonal & neuronal neuropathies; Balo disease; Behcet's disease; bullous pemphigoid; cardiomyopathy; Castleman disease; celiac disease; Chagas disease; chronic inflammatory demyelinating polyneuropathy (CIDP); chronic recurrent multifocal ostomyelitis (CRMO); Churg-Strauss syndrome; cicatricial pemphigoid/benign mucosal pemphigoid; Crohn's disease; Cogans syndrome; cold agglutinin disease; congenital heart block; Coxsackie myocarditis; CREST disease; essential mixed cryoglobulinemia; demyelinating neuropathies; dermatitis herpetiformis; dermatomyositis; Devic's disease (neuromyelitis optica); discoid lupus; Dressler's syndrome; endometriosis; eosinophilic esophagitis; eosinophilic fasciitis; erythema nodosum; experimental allergic encephalomyelitis; Evans syndrome; fibrosing alveolitis; giant cell arteritis (temporal arteritis); giant cell myocarditis; glomerulonephritis; Goodpasture's syndrome; granulomatosis with polyangiitis (GPA) (formerly called Wegener's granulomatosis); Graves' disease; Guillain-Barre syndrome; Hashimoto's encephalitis; Hashimoto's thyroiditis; hemolytic anemia; Henoch-Schonlein purpura; herpes gestationis; hypogammaglobulinemia; idiopathic thrombocytopenic purpura (ITP); IgA nephropathy; IgG4-related sclerosing disease; immunoregulatory lipoproteins; inclusion body myositis; interstitial cystitis; juvenile arthritis; juvenile diabetes (type 1 diabetes); juvenile myositis; Kawasaki syndrome; Lambert-Eaton syndrome; leukocytoclastic vasculitis; lichen planus; lichen sclerosus; ligneous conjunctivitis; linear IgA disease (LAD); lupus (SLE); lyme disease, chronic; Meniere's disease; microscopic polyangiitis; mixed connective tissue disease (MCTD); Mooren's ulcer; Mucha-Habermann disease; multiple sclerosis; myasthenia gravis; myositis; narcolepsy; neuromyelitis optica (Devic's); neutropenia; ocular cicatricial pemphigoid; optic neuritis; palindromic rheumatism; PANDAS (Pediatric Autoimmune Neuropsychiatric Disorders Associated with *Streptococcus*); paraneoplastic cerebellar degeneration; paroxysmal nocturnal hemoglobinuria (PNH); Parry Romberg syndrome; Parsonnage-Turner syndrome; pars planitis (peripheral uveitis); pemphigus; peripheral neuropathy; perivenous encephalomyelitis; pernicious anemia; POEMS syndrome; polyarteritis nodosa; type I, II, & III autoimmune polyglandular syndromes; polymyalgia rheumatic; polymyositis; postmyocardial infarction syndrome; postpericardiotomy syndrome; progesterone dermatitis; primary biliary cirrhosis; primary sclerosing cholangitis; psoriasis; psoriatic arthritis; idiopathic pulmonary fibrosis; pyoderma gangrenosum; pure red cell aplasia; Raynauds phenomenon; reactive arthritis; reflex sympathetic dystrophy; Reiter's syndrome; relapsing polychondritis; restless legs syndrome; retroperitoneal fibrosis; rheumatic fever; rheumatoid arthritis; sarcoidosis; Schmidt syndrome; scleritis; scleroderma; Sjogren's syndrome; sperm & testicular autoimmunity; stiff person syndrome; subacute bacterial endocarditis (SBE); Susac's syndroms; sympathetic ophthalmia; Takayasu's arteritis; temporal arteritis/giant cell arteritis; thrombocytopenic purpura (TTP); Tolosa-Hunt syndrome; transverse myelitis; type 1 diabetes; ulcerative colitis; undifferentiated connective tissue disease (UCTD); uveitis; vasculitis; vesiculobullous dermatosis; vitiligo; and Wegener's granulomatosis (now termed granulomatosis with polyangiitis (GPA).

According to a further aspect of the invention, there is provided a method of treating an autoimmune disease in a subject, comprising administering the protein of the invention to a subject having at least one autoimmune disease.

It will be appreciated that the protein of the invention can be administered as the sole therapeutic agent or it can be administered in combination therapy with one of more other compounds (or therapies) for the treatment of an autoimmune disease.

Thus, according to a further aspect of the invention there is provided a pharmaceutical composition comprising the protein as defined herein in combination with one or more additional therapeutic agents.

For the treatment of an autoimmune disease, the protein of the invention may be advantageously employed in combination with one or more other medicinal agents, more particularly, with one or more immunosuppressive agents or adjuvants in immunosuppression therapy.

Examples of other therapeutic agents or treatments that may be administered together (whether concurrently or at different time intervals) with the compounds of the invention include but are not limited to: azathioprine; methotrexate; cyclosporine; monoclonal antibodies (basiliximab, daclizumab, and muromonab); and corticosteroids.

Each of the therapeutic agents present in the combinations of the invention may be given in individually varying dose schedules and via different routes. Additionally, the posology of each of the two or more agents may differ: each may be administered at the same time or at different times. A person skilled in the art would know through his or her common general knowledge the dosing regimes and combination therapies to use. For example, the protein of the invention may be used in combination with one or more other agents which are administered according to their existing combination regimen.

Generally, the proteins disclosed herein will be utilised in purified form together with pharmacologically appropriate excipients or carriers. Typically, these excipients or carriers include aqueous or alcoholic/aqueous solutions, emulsions or suspensions, including saline and/or buffered media. Parenteral vehicles include sodium chloride solution, Ringer's dextrose, dextrose and sodium chloride and lactated Ringer's. Suitable physiologically acceptable adjuvants, if necessary to keep a polypeptide complex in suspension, may be chosen from thickeners such as carboxymethylcellulose, polyvinylpyrrolidone, gelatin and alginates.

The route of administration of pharmaceutical compositions according to the invention may be any of those commonly known to those of ordinary skill in the art. For therapy, including without limitation immunotherapy, the proteins of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. The dosage and frequency of administration will depend on the age, sex and condition of the patient, concurrent administration of other drugs, counterindications and other parameters to be taken into account by the clinician.

The proteins of the invention can be lyophilised for storage and reconstituted in a suitable carrier prior to use. This technique has been shown to be effective and art-known lyophilisation and reconstitution techniques can be employed. It will be appreciated by those skilled in the art that lyophilisation and reconstitution can lead to varying degrees of activity loss and that levels may have to be adjusted upward to compensate.

The following studies and protocols illustrate embodiments of the methods described herein.

Example 1: Manufacture of Mutant and Wild Type CD200-Fc Molecules

Gene Synthesis

A DNA sequence encoding mutant or wild-type human CD200 residues 1-231 of Uniprot P412178 (OX2G_Human), which includes an N-terminal signal sequence, was fused at the C-terminus to IgG1 Fc, residues 99-330 of P01857 (IHG1_Human), with a linker sequence of GGGGSGGGGS (SEQ ID NO: 11) between the 2 protein domains. Gene synthesis was carried out at GeneArt for the wild type and mutant constructs.

The expression constructs were made using the mammalian expression vector pcDNA3.4, with 5' Hind III and 3'Xho. An internal Bam HI was introduced to facilitate Fc domain swapping.

Midi Prep

Upon receipt, the lyophilized DNA constructs of the CD200-Fc target proteins (both wild-type and mutant CD200-Fc proteins) were suspended in 50 µl of MQ and transformed DH 5α cells. A single colony of each target protein was selected and inoculated into 5.0 ml of LB containing ampicillin. Next, DNA from 2.0 ml of culture was isolated for confirmation and resolved by Agarose gel electrophoresis. The constructs were confirmed by digesting the DNA with Hind III and XhoI. Each mutant or wild-type construct was cultured into 100 ml of LB for the midi scale DNA preparation. The DNA was isolated using the purelink Hipure plasmid midiprep kit.

Protein Expression

The CD200-Fc target proteins were manufactured using the Thermo Fisher Gibco™ ExpiCHO™ expression system according to the manufacturer's instructions for a 25 ml culture volume. The media supernatant containing the expressed CD200-Fc was collected and stored at −80° C. until use.

Protein Purification

Buffer exchange was performed using a Hiprep desalting column (XK26/10) packed with 53 ml of SephadexG25 to condition the media for affinity column purification. The desalting columns were equilibrated with Buffer A (150 mM NaCl containing 20 mM Sodium phosphate pH 7.4) on an AKTA explorer platform. 30 ml of clarified culture media was loaded onto two desalting columns connected in series at a rate of 1 ml/min. The protein was eluted at a rate of 2 ml/min and collected in fractions. Fractions showing a maximum absorbance and pH 7.4-7.2 were pooled. Fractions exhibiting a lower pH were rejected. Following the desalting the samples were diluted to make up approximately 45 ml of wild-type or mutant CD200-Fc supernatant. All of the purification procedures were performed on ice at 4° C.

The column was washed with 10 column volumes of Buffer A (10 ml of 20 mM sodium phosphate pH 7.4, 150 mM NaCl). CD200-Fc Protein was eluted with a pH 7.4-3.5 gradient over 10-column volumes using 20 mM Sodium Phosphate pH 7.4, 150 mM NaCl and 100 mM Citrate buffer pH 3.5 in a linear gradient. The CD200-Fc fractions comprising the 140 kDa dimeric form of the protein were isolated based on SDS PAGE data. The protein buffer was exchanged using an Amicon ultra centricon with a 10 kDa cut-off and the protein concentrated to around 1 mg/ml.

Figure 2:
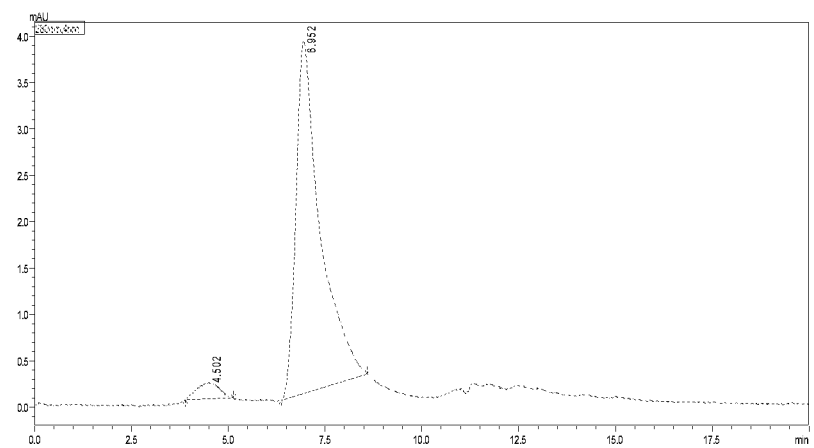
FIG. 2: A: Size Exclusion Chromatograph of K130Y.
B: Size Exclusion Chromatograph of I131Y.
Figure 2:
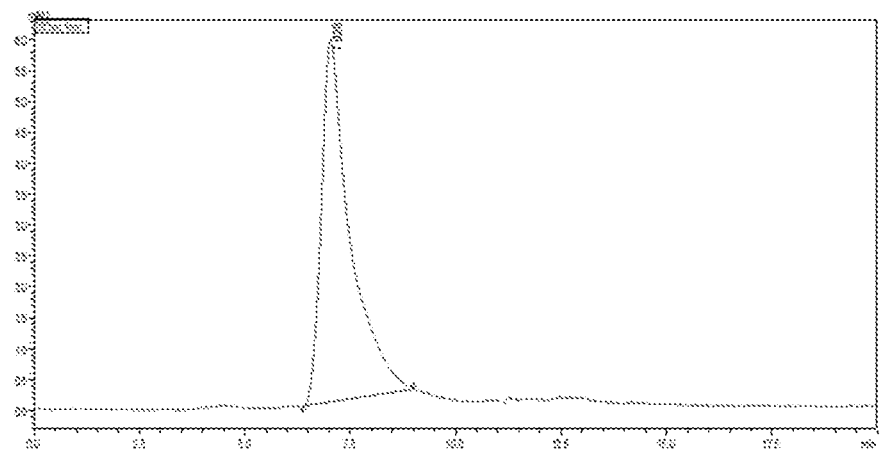

FIG. 1 shows SGS gels of wild type CD200-Fc, K130Y and I131Y. Size exclusion chromatography was used to demonstrate that the prepared CD200-Fc proteins did not form aggregates in solution prior to performing the binding analysis (FIG. 2).

Example 2: Binding Analysis of the Wild-Type and Mutant CD200-Fc Molecules

Biacore experiments were performed by Syngene International Ltd. (Biocon Park, Plot No 2&3, Bommasandra Industrial Area, Bommasadra-Jigani Link Road, Bangalore—560099, India).

Assay Principles

BIAcore instrumentation uses an optical method, Surface Plasmon Resonance (SPR), to measure the binding characteristics of two interacting molecules; in this case wild-type CD200-Fc or CD200-Fc mutants binding to the CD200 receptor (CD200R). The technique measures changes in the refractive index of one of the two interacting molecules captured on a chip (sensor) when the second molecule is flowed in solution over the captured partner. In these experiments CD200-Fc was immobilized on the chip (sensor) surface and CD200R was injected in an aqueous buffer over the captured CD200-Fc under continuous flow conditions. Changes in the CD200-Fc refractive index following CD200R binding were measured in real time and the result plotted as response units (RUs) versus time to generate sensorgrams (FIGS. 5a and 5b).

Instrumentation and Reagents

The experiments were performed on a GE Healthcare BIAcore T200. Table 1 details the reagents used in developing and performing the assay.

TABLE 1

Reagents used in the course of the BIAcore experiments

| Sl. No. | Product Description | Vendor | Catalogue No. |
|---|---|---|---|
| 1 | Human Antibody Capture Kit | GE Healthcare | BR1008-39 |
| 2 | Recombinant HumanCD200R, His tagged | Creative Biomart | CD200R1-320H |
| 3 | Recombinant HumanCD200, Fc-tagged | Creative Biomart | CD200-165H |
| 4 | Recombinant Mouse CD200 Protein, Fc Chimera | Creative Biomart | CD200-982M |
| 5 | Trastuzumab | Roche | N/A |

CD200-Fc Immobilization

Figure 3:
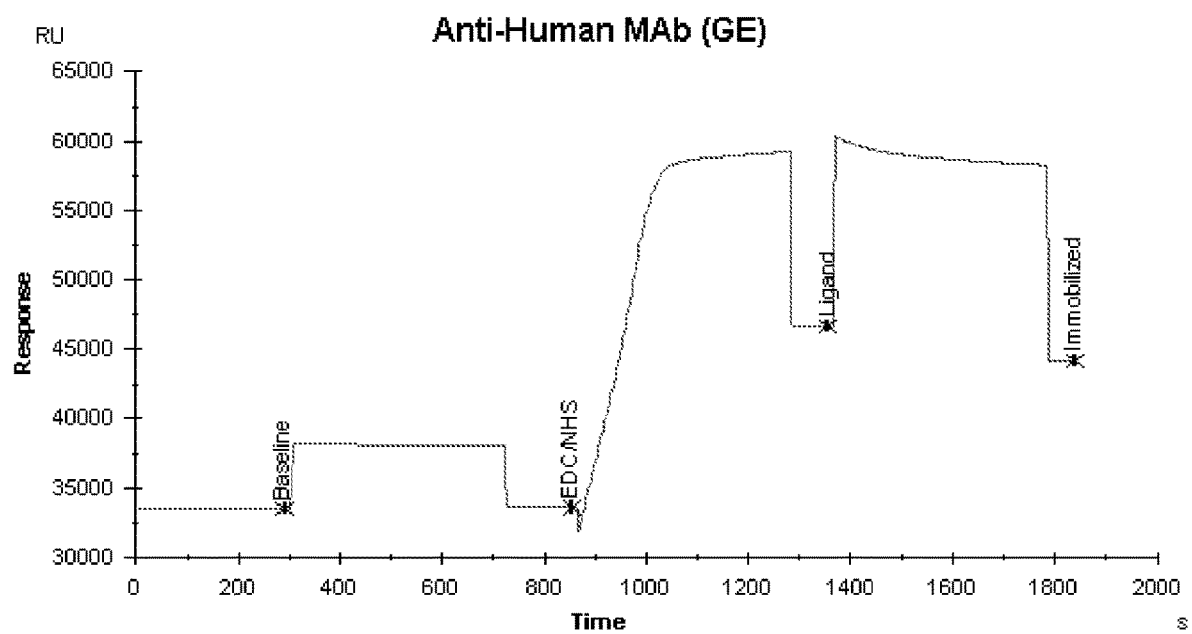
FIG. 3: Immobilization of Anti-human Fc antibody on the sensor chip surface.
Figure 4:
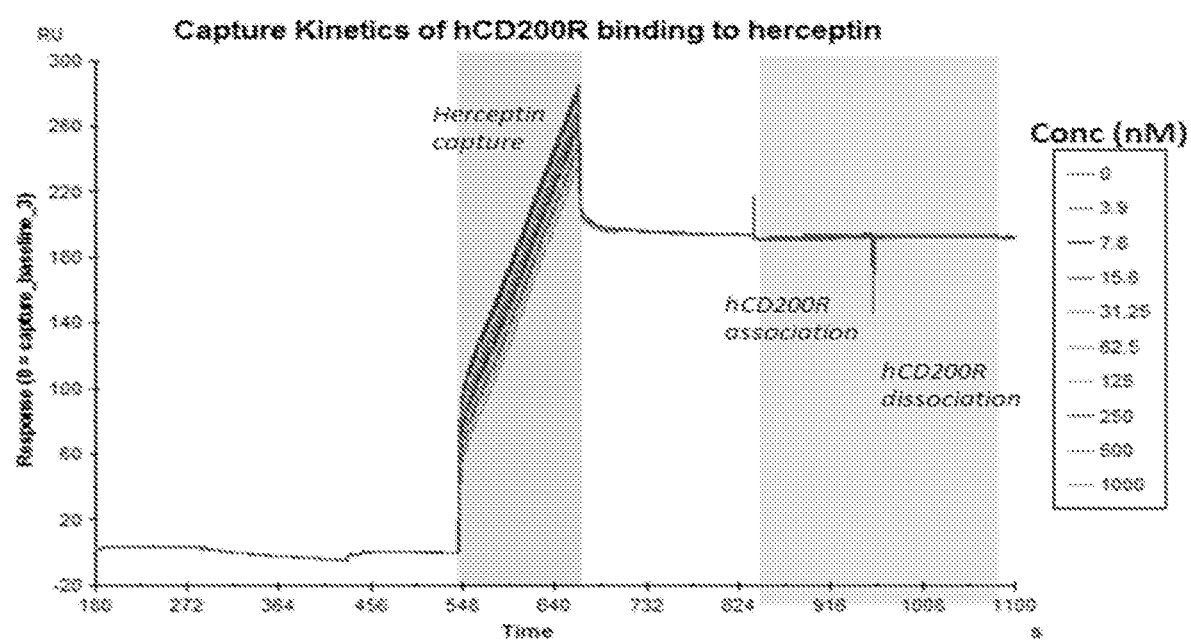
FIG. 4: Herceptin capture and hCD200R association/dissociation.

Anti-human Fc was covalently immobilized on a BIAcore CM5 sensor chip by amine coupling using a GE Healthcare kit following the manufacturer's instructions. Maximum immobilization target was set between 10000-15000 RU. FIG. 3 shows capture of the anti-human Fc antibody on the chip surface. Flow cell 1 was used as a reference, with no immobilized ligand, to permit deduction of non-specific binding to the chip surface. The Fc-ligands were diluted to 0.5 μg/mL in BIAcore running buffer (HBS-EP+: 10 mM HEPES buffered saline containing 2 mM EDTA and 0.05% surfactant P-20). In the final immobilization step, wild-type CD200-Fc, mutant CD200-Fc and un-related control protein (Herceptin/Trastuzumab) were passed over the chip (using flow cells 2, 3 and 4 respectively), for 120 seconds, at a concentration giving rise to a minimum of 250 response units (RU), followed by stabilization of the surface for 120 seconds in running buffer. The CD200-Fc capture procedure was repeated for every CD200R concentration. FIG. 4 shows that, as expected, the CD200 receptor does not bind to Herceptin immobilized on the chip surface.

Passage of CD200R Over the CD200-Fc-Bound Chip Surface

Following capture of the Fc-tagged proteins, CD200R (at different concentrations) was flowed over the captured CD200-Fc and control proteins for 120 seconds (to observe association), followed by 120 seconds of running buffer (to observe dissociation). The chip surface was then regenerated using 10 mM Glycine-HCl (pH 2) for 30 seconds (30 μL/min flow rate) followed by stabilization of the surface for 60 seconds with BIAcore running buffer before the next cycle. All CD200R concentrations were run in duplicate at the following concentrations: 1 μM, 500 nM, 250 nM, 125 nM, 62.5 nM, 31.25 nM, 15.6 and 0 nM.

Data Analysis

The results were represented in sensorgrams plotted as response or resonance units (RUs) versus time. The experimental sensorgrams were analyzed in BIAevaluation software version 1.0 (GE Healthcare). Curve fitting was carried out using a 1:1 Langmuir binding model. Rate equations using standard parameters (e.g. ligand concentration, time) were used for iterative curve fitting. Closeness of fit was determined by algorithms provided by the manufacturer in the BIAevaluation software version 1.0.

Results

FIG. 4 shows that, as expected, the CD200 receptor does not bind to Herceptin immobilized on the chip surface. FIG. 5 shows sensorgrams for CD200 receptor binding to wild-type CD200-Fc (FIG. 5A) and K130Y mutant CD200-Fc (FIG. 5B). It is clear from comparison of the sensorgrams in FIG. 5 that K130Y binds to the CD200 receptor with greater affinity and a slower off rate than wild-type CD200-Fc. Table 2 records the on rates ($M^{-1}s^{-1}$), off rates ($s^{-1}$) and binding affinity values (nM) for wild-type and mutant CD200-Fc molecules: WT, K130Y, I131Y, G129I, F128R, N81K. Half-lives were calculated using the relationship $t_{1/2}$ (s)=0.693/$k_{off}(s^{-1})$.

TABLE 2

On rates ($M^{-1}s^{-1}$), off rates ($s^{-1}$) and binding affinity values (nM) for mutant CD200-Fc molecules

| SEQ ID NO: | Mutation | On-rate ($M^{-1}s^{-1}$) | Off-rate ($s^{-1}$) | Affinity (nM) | t ½ (s) |
|---|---|---|---|---|---|
| SEQ ID NO: 5 | WT | 2.4E+05 | 2.7E−02 | 111.00 | 25.6 |
| SEQ ID NO: 6 | K130Y | 4.0E+05 | 3.2E−03 | 8.07 | 216.6 |
| SEQ ID NO: 7 | I131Y | 1.8E+05 | 9.1E−03 | 49.00 | 76.6 |
| SEQ ID NO: 8 | G129I | 1.58 E5 | 1.7E−02 | 108.00 | 40.8 |
| SEQ ID NO: 9 | F128R | 1.63E 5 | 1.8E−02 | 109 | 39.2 |
| SEQ ID NO: 10 | N81K | 2.07 E5 | 2.1E−02 | 101 | 32.7 |

Example 3: Analysis Using a Functional Cellular Model

An oxidative burst assay was performed by GVK Biosciences Private Limited (Campus MLR 1, Survey Nos. 125 & 126, IDA Mallapur, Hyderabad—500076, India).

Oxidative burst was measured in isolated human neutrophils with a commercial flow cytometric-based kit (CAY601130, Cayman Chemicals, Michigan, 48108, USA) according to the manufacturer's instructions. The assay quantifies oxidative burst by flow cytometry following initiation of oxidative burst using Phorbol 12-Myristate 13-Acetate (PMA). Oxidative activity was measured using Dihydrorhodamine 123, a cell permeable, non-fluorescent dye, which is converted to the fluorescent compound rhodamine 123 by oxidative activity following PMA stimulation. Samples with PMA stimulus and without CD200-Fc incubation provided the positive control. Samples without PMA stimulus served as the negative background control.

Assay Protocol

Human neutrophils were isolated from peripheral blood by ficoll-paque separation and dextran sedimentation. The cells were suspended in assay buffer (500 mL RPMI basal medium, 5 g BS and 500 uL of 1 M Calcium Chloride) at a concentration of $1 \times 10^6$ cells/mL. The cells were incubated for 30 minutes at 37° C. in a water bath with the reference molecule (wild-type CD200-Fc) or CD200-Fc mutants. Next a 10 μL volume of 10× working stock of Dihydrorhodamine 123 was added to the cells which were incubated for 15 minutes at 37° C. in the water bath. The cells were stimulated with 200 nM of PMA (1 mM stock) and incubated for a further 45 minutes at 37° C. in the water bath. Following the final incubation step, the cells were centrifuged (500×g) for 10 minutes at room temperature. The supernatant was discarded and the pellet was re-suspended in 0.5 mL of assay buffer. The cells were analyzed by flow cytometry (BD FACSVerse, BD Biosciences, New Jersey, US). The data was plotted using the mean fluorescent intensity values of cells treated with PMA alone and compared with cells treated with PMA and test compounds (wild-type CD200-Fc or mutant CD200-Fc). GraphPad Prism version 6.0 was used to perform the data analysis. The neutrophil cluster was gated in the analysis program using forward and side scatter (FSC vs SSC) to ensure that the appropriate cell population data were collected. Finally, the fluorescence histograms were analyzed to quantify the effect of wild-type and mutant CD200-Fc proteins on oxidative burst.

Data Analysis

CD200-Fc mediated inhibition of oxidative burst was measured using the formula:

Percent inhibition=100−(100×(Average Test Compound Counts−Average Negative Control Counts)/(Average Positive Control Counts−Average Negative Control Counts)

Counts in the above formula are derived from Mean Fluorescent Intensity Values from the gated cell population. The data was analyzed for statistical significance by One-way ANOVA with a Bonferroni post-test comparing all the columns.

Results

Figure 6:
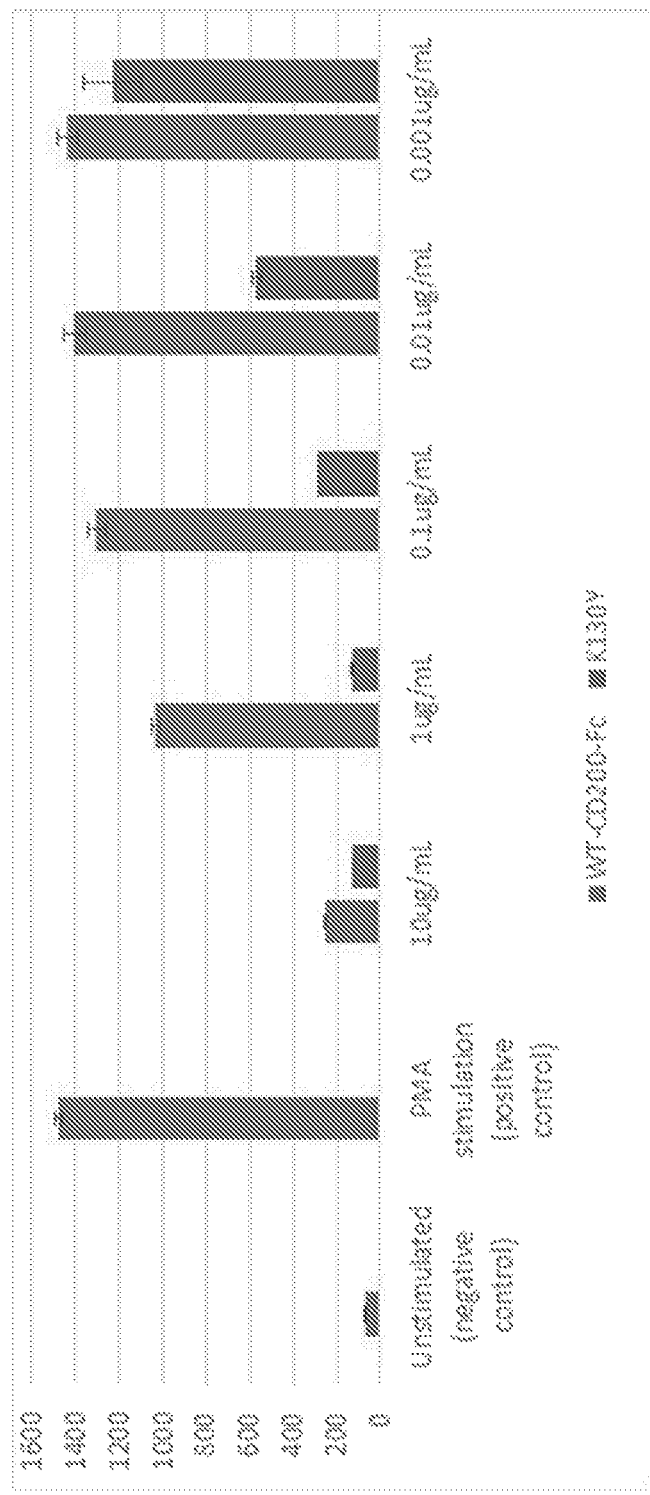
FIG. 6: Dose response results comparing the inhibition of PMA stimulated oxidative burst in isolated human neutrophils by wild-type CD200-Fc and K130Y.

Table 3 details mean fluorescent intensity values from the gated cell population for wild-type CD200-Fc, K130Y and positive and negative controls. FIG. 6 compares the effects of wild-type CD200-Fc and K130Y in the oxidative burst assay.

It can readily be seen from FIG. 6 that the K130Y mutant CD200-Fc inhibits PMA stimulated oxidative burst in the oxidative burst assay more potently and at lower doses than wild-type CD200-Fc. Furthermore, this increase in functional activity can be attributed to the K130Y mutation since the two proteins are identical save for the K130Y mutation. It is recognised that neutrophils are found in high number in inflamed tissue (for example, rheumatoid joints and synovial fluid) and furthermore that they have a huge potential to directly inflict damage to tissue, bone and cartilage via the secretion of proteases and toxic oxygen metabolites, as well as driving inflammation through antigen presentation and secretion of cytokines, chemokines, prostaglandins and leukotrienes (Wright, H. L., et al., (2010) *Rheumatology* 49, 1618-1631). Agents which inhibit neutrophil activation can therefore be expected to function as useful treatments for inflammatory and autoimmune diseases whose pathology is mediated wholly or in part by aberrant neutrophil activation.

TABLE 3

Mean fluorescent intensity values from the gated cell population for wild-type CD200-Fc, K130Y and positive and negative controls. SD values from duplicate experiments in parenthesis.

|  | WT-CD200-Fc | K130Y |
| --- | --- | --- |
| 10 ug/mL | 248.5 (126) | 126 (2.8) |
| 1 ug/mL | 1033.5 (19.1) | 133.5 (4.9) |
| 0.1 ug/mL | 1304.5 (38.9) | 287.5 (2.1) |
| 0.01 ug/mL | 1407 (50.9) | 568.5 (17.7) |
| 0.001 ug/mL | 1437 (48.1) | 1229.5 (129.4) |
| Unstimulated (negative control) | 68.5 (6.4) | |
| PMA stimulation (positive control) | 1480.5 (16.3) | |

The invention claimed is:

1. A mutated CD200 protein, comprising an amino acid sequence with at least about 99% sequence identity to SEQ ID NO: 1, wherein said amino acid sequence additionally comprises at least one substitution mutation selected from K130Y and I131Y, and wherein the mutated CD200 protein is an agonist of the CD200 receptor.

2. The protein of claim 1, which comprises one or more additional mutations selected from G129I, F128R, and N81K.

3. The protein of claim 1, comprising the sequence of SEQ ID NO: 12 or SEQ ID NO: 13.

4. A mutated CD200 protein extracellular domain, comprising: an amino acid sequence with at least about 99% sequence identity to SEQ ID NO: 2,
 wherein said amino acid sequence additionally comprises at least one substitution mutation selected from K130Y and I131Y, wherein residue positions 130 and 131 correspond to residue numbering of SEQ ID NO: 1,
 wherein the mutated CD200 protein extracellular domain binds the CD200 receptor, and
 wherein the mutated CD200 protein is an agonist of the CD200 receptor.

5. The protein of claim 4, comprising the sequence of SEQ ID NO: 3 or SEQ ID NO: 4.

6. A fusion protein, comprising: the mutated CD200 protein extracellular domain of claim 4 fused to a non-CD200 protein or peptide that does not bind a CD200 receptor, wherein an optional linker portion links the mutated CD200 protein extracellular domain and the non-CD200 protein or peptide.

7. The fusion protein of claim 6, wherein said linker portion is a peptide comprising between 1 and 15 amino acids.

8. The fusion protein of claim 6, wherein said non-CD200 protein or peptide is an antibody or fragment thereof.

9. The fusion protein of claim 6, wherein said non-CD200 protein or peptide is an Fc fragment.

10. The fusion protein of claim 6, comprising the sequence of SEQ ID NO: 6 or SEQ ID NO: 7.

11. A polynucleotide encoding a protein of claim 1.

12. A pharmaceutical composition comprising the protein of claim 1.

13. A method for the treatment of autoimmune disease, comprising: providing the pharmaceutical composition of claim 12.

14. A method for the treatment of autoimmune disease, comprising: providing the protein of claim 1.

15. The fusion protein of claim 7, wherein said non-CD200 protein or peptide is an antibody or fragment thereof.

16. A polynucleotide encoding a protein of claim 4.

17. A pharmaceutical composition comprising the protein of claim 4.

18. A method for the treatment of autoimmune disease, comprising: providing the pharmaceutical composition of claim 17.

19. A method for the treatment of autoimmune disease, comprising: providing the protein of claim 4.

* * * * *

SEQUENCE LISTING

```
<160> NUMBER OF SEQ ID NOS: 13

<210> SEQ ID NO 1
<211> LENGTH: 278
<212> TYPE: PRT
<213> ORGANISM: Homo sapien

<400> SEQUENCE: 1

Met Glu Arg Leu Val Ile Arg Met Pro Phe Ser His Leu Ser Thr Tyr
1               5                   10                  15

Ser Leu Val Trp Val Met Ala Ala Val Val Leu Cys Thr Ala Gln Val
            20                  25                  30

Gln Val Val Thr Gln Asp Glu Arg Glu Gln Leu Tyr Thr Pro Ala Ser
        35                  40                  45

Leu Lys Cys Ser Leu Gln Asn Ala Gln Glu Ala Leu Ile Val Thr Trp
    50                  55                  60

Gln Lys Lys Lys Ala Val Ser Pro Glu Asn Met Val Thr Phe Ser Glu
65                  70                  75                  80

Asn His Gly Val Val Ile Gln Pro Ala Tyr Lys Asp Lys Ile Asn Ile
                85                  90                  95

Thr Gln Leu Gly Leu Gln Asn Ser Thr Ile Thr Phe Trp Asn Ile Thr
            100                 105                 110
```

-continued

Leu Glu Asp Glu Gly Cys Tyr Met Cys Leu Phe Asn Thr Phe Gly Phe
            115                 120                 125

Gly Lys Ile Ser Gly Thr Ala Cys Leu Thr Val Tyr Val Gln Pro Ile
    130                 135                 140

Val Ser Leu His Tyr Lys Phe Ser Glu Asp His Leu Asn Ile Thr Cys
145                 150                 155                 160

Ser Ala Thr Ala Arg Pro Ala Pro Met Val Phe Trp Lys Val Pro Arg
                165                 170                 175

Ser Gly Ile Glu Asn Ser Thr Val Thr Leu Ser His Pro Asn Gly Thr
            180                 185                 190

Thr Ser Val Thr Ser Ile Leu His Ile Lys Asp Pro Lys Asn Gln Val
        195                 200                 205

Gly Lys Glu Val Ile Cys Gln Val Leu His Leu Gly Thr Val Thr Asp
    210                 215                 220

Phe Lys Gln Thr Val Asn Lys Gly Tyr Trp Phe Ser Val Pro Leu Leu
225                 230                 235                 240

Leu Ser Ile Val Ser Leu Val Ile Leu Val Leu Ile Ser Ile Leu
                245                 250                 255

Leu Tyr Trp Lys Arg His Arg Asn Gln Asp Arg Gly Glu Leu Ser Gln
            260                 265                 270

Gly Val Gln Lys Met Thr
        275

<210> SEQ ID NO 2
<211> LENGTH: 201
<212> TYPE: PRT
<213> ORGANISM: Homo sapien

<400> SEQUENCE: 2

Gln Val Gln Val Val Thr Gln Asp Glu Arg Glu Gln Leu Tyr Thr Pro
1               5                   10                  15

Ala Ser Leu Lys Cys Ser Leu Gln Asn Ala Gln Glu Ala Leu Ile Val
            20                  25                  30

Thr Trp Gln Lys Lys Lys Ala Val Ser Pro Glu Asn Met Val Thr Phe
        35                  40                  45

Ser Glu Asn His Gly Val Val Ile Gln Pro Ala Tyr Lys Asp Lys Ile
    50                  55                  60

Asn Ile Thr Gln Leu Gly Leu Gln Asn Ser Thr Ile Thr Phe Trp Asn
65                  70                  75                  80

Ile Thr Leu Glu Asp Glu Gly Cys Tyr Met Cys Leu Phe Asn Thr Phe
                85                  90                  95

Gly Phe Gly Lys Ile Ser Gly Thr Ala Cys Leu Thr Val Tyr Val Gln
            100                 105                 110

Pro Ile Val Ser Leu His Tyr Lys Phe Ser Glu Asp His Leu Asn Ile
        115                 120                 125

Thr Cys Ser Ala Thr Ala Arg Pro Ala Pro Met Val Phe Trp Lys Val
    130                 135                 140

Pro Arg Ser Gly Ile Glu Asn Ser Thr Val Thr Leu Ser His Pro Asn
145                 150                 155                 160

Gly Thr Thr Ser Val Thr Ser Ile Leu His Ile Lys Asp Pro Lys Asn
                165                 170                 175

Gln Val Gly Lys Glu Val Ile Cys Gln Val Leu His Leu Gly Thr Val
            180                 185                 190

Thr Asp Phe Lys Gln Thr Val Asn Lys 195                 200

<210> SEQ ID NO 3
<211> LENGTH: 201
<212> TYPE: PRT
<213> ORGANISM: Artificial
<220> FEATURE:
<223> OTHER INFORMATION: Synthesized

<400> SEQUENCE: 3

Gln Val Gln Val Val Thr Gln Asp Glu Arg Glu Gln Leu Tyr Thr Pro
1               5                   10                  15

Ala Ser Leu Lys Cys Ser Leu Gln Asn Ala Gln Glu Ala Leu Ile Val
            20                  25                  30

Thr Trp Gln Lys Lys Lys Ala Val Ser Pro Glu Asn Met Val Thr Phe
        35                  40                  45

Ser Glu Asn His Gly Val Val Ile Gln Pro Ala Tyr Lys Asp Lys Ile
    50                  55                  60

Asn Ile Thr Gln Leu Gly Leu Gln Asn Ser Thr Ile Thr Phe Trp Asn
65                  70                  75                  80

Ile Thr Leu Glu Asp Glu Gly Cys Tyr Met Cys Leu Phe Asn Thr Phe
                85                  90                  95

Gly Phe Gly Tyr Ile Ser Gly Thr Ala Cys Leu Thr Val Tyr Val Gln
            100                 105                 110

Pro Ile Val Ser Leu His Tyr Lys Phe Ser Glu Asp His Leu Asn Ile
        115                 120                 125

Thr Cys Ser Ala Thr Ala Arg Pro Ala Pro Met Val Phe Trp Lys Val
    130                 135                 140

Pro Arg Ser Gly Ile Glu Asn Ser Thr Val Thr Leu Ser His Pro Asn
145                 150                 155                 160

Gly Thr Thr Ser Val Thr Ser Ile Leu His Ile Lys Asp Pro Lys Asn
                165                 170                 175

Gln Val Gly Lys Glu Val Ile Cys Gln Val Leu His Leu Gly Thr Val
            180                 185                 190

Thr Asp Phe Lys Gln Thr Val Asn Lys
        195                 200

<210> SEQ ID NO 4
<211> LENGTH: 201
<212> TYPE: PRT
<213> ORGANISM: Artificial
<220> FEATURE:
<223> OTHER INFORMATION: Synthesized

<400> SEQUENCE: 4

Gln Val Gln Val Val Thr Gln Asp Glu Arg Glu Gln Leu Tyr Thr Pro
1               5                   10                  15

Ala Ser Leu Lys Cys Ser Leu Gln Asn Ala Gln Glu Ala Leu Ile Val
            20                  25                  30

Thr Trp Gln Lys Lys Lys Ala Val Ser Pro Glu Asn Met Val Thr Phe
        35                  40                  45

Ser Glu Asn His Gly Val Val Ile Gln Pro Ala Tyr Lys Asp Lys Ile
    50                  55                  60

Asn Ile Thr Gln Leu Gly Leu Gln Asn Ser Thr Ile Thr Phe Trp Asn
65                  70                  75                  80

Ile Thr Leu Glu Asp Glu Gly Cys Tyr Met Cys Leu Phe Asn Thr Phe
                85                  90                  95

```
Gly Phe Gly Lys Tyr Ser Gly Thr Ala Cys Leu Thr Val Tyr Val Gln
            100                 105                 110

Pro Ile Val Ser Leu His Tyr Lys Phe Ser Glu Asp His Leu Asn Ile
        115                 120                 125

Thr Cys Ser Ala Thr Ala Arg Pro Ala Pro Met Val Phe Trp Lys Val
    130                 135                 140

Pro Arg Ser Gly Ile Glu Asn Ser Thr Val Thr Leu Ser His Pro Asn
145                 150                 155                 160

Gly Thr Thr Ser Val Thr Ser Ile Leu His Ile Lys Asp Pro Lys Asn
                165                 170                 175

Gln Val Gly Lys Glu Val Ile Cys Gln Val Leu His Leu Gly Thr Val
            180                 185                 190

Thr Asp Phe Lys Gln Thr Val Asn Lys
        195                 200

<210> SEQ ID NO 5
<211> LENGTH: 473
<212> TYPE: PRT
<213> ORGANISM: Artificial
<220> FEATURE:
<223> OTHER INFORMATION: Synthesized

<400> SEQUENCE: 5

Met Glu Arg Leu Val Ile Arg Met Pro Phe Ser His Leu Ser Thr Tyr
1               5                   10                  15

Ser Leu Val Trp Val Met Ala Ala Val Val Leu Cys Thr Ala Gln Val
            20                  25                  30

Gln Val Val Thr Gln Asp Glu Arg Glu Gln Leu Tyr Thr Pro Ala Ser
        35                  40                  45

Leu Lys Cys Ser Leu Gln Asn Ala Gln Glu Ala Leu Ile Val Thr Trp
    50                  55                  60

Gln Lys Lys Lys Ala Val Ser Pro Glu Asn Met Val Thr Phe Ser Glu
65                  70                  75                  80

Asn His Gly Val Val Ile Gln Pro Ala Tyr Lys Asp Lys Ile Asn Ile
                85                  90                  95

Thr Gln Leu Gly Leu Gln Asn Ser Thr Ile Thr Phe Trp Asn Ile Thr
            100                 105                 110

Leu Glu Asp Glu Gly Cys Tyr Met Cys Leu Phe Asn Thr Phe Gly Phe
        115                 120                 125

Gly Lys Ile Ser Gly Thr Ala Cys Leu Thr Val Tyr Val Gln Pro Ile
    130                 135                 140

Val Ser Leu His Tyr Lys Phe Ser Glu Asp His Leu Asn Ile Thr Cys
145                 150                 155                 160

Ser Ala Thr Ala Arg Pro Ala Pro Met Val Phe Trp Lys Val Pro Arg
                165                 170                 175

Ser Gly Ile Glu Asn Ser Thr Val Thr Leu Ser His Pro Asn Gly Thr
            180                 185                 190

Thr Ser Val Thr Ser Ile Leu His Ile Lys Asp Pro Lys Asn Gln Val
        195                 200                 205

Gly Lys Glu Val Ile Cys Gln Val Leu His Leu Gly Thr Val Thr Asp
    210                 215                 220

Phe Lys Gln Thr Val Asn Lys Gly Gly Gly Ser Gly Gly Gly
225                 230                 235                 240

Ser Glu Pro Lys Ser Cys Asp Lys Thr His Thr Cys Pro Pro Cys Pro
                245                 250                 255
```

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
            275                 280                 285

Val Val Asp Val Ser His Glu Asp Pro Glu Val Lys Phe Asn Trp Tyr
290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
            325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
            355                 360                 365

Pro Arg Glu Pro Gln Val Tyr Thr Leu Pro Pro Ser Arg Asp Glu Leu
            370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
            405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
            435                 440                 445

Phe Ser Cys Ser Val Met His Glu Ala Leu His Asn His Tyr Thr Gln
            450                 455                 460

Lys Ser Leu Ser Leu Ser Pro Gly Lys
465                 470

<210> SEQ ID NO 6
<211> LENGTH: 473
<212> TYPE: PRT
<213> ORGANISM: Artificial
<220> FEATURE:
<223> OTHER INFORMATION: Synthesized

<400> SEQUENCE: 6

Met Glu Arg Leu Val Ile Arg Met Pro Phe Ser His Leu Ser Thr Tyr
1               5                   10                  15

Ser Leu Val Trp Val Met Ala Ala Val Val Leu Cys Thr Ala Gln Val
            20                  25                  30

Gln Val Val Thr Gln Asp Glu Arg Glu Gln Leu Tyr Thr Pro Ala Ser
            35                  40                  45

Leu Lys Cys Ser Leu Gln Asn Ala Gln Glu Ala Leu Ile Val Thr Trp
50                  55                  60

Gln Lys Lys Lys Ala Val Ser Pro Glu Asn Met Val Thr Phe Ser Glu
65                  70                  75                  80

Asn His Gly Val Val Ile Gln Pro Ala Tyr Lys Asp Lys Ile Asn Ile
            85                  90                  95

Thr Gln Leu Gly Leu Gln Asn Ser Thr Ile Thr Phe Trp Asn Ile Thr
            100                 105                 110

Leu Glu Asp Glu Gly Cys Tyr Met Cys Leu Phe Asn Thr Phe Gly Phe
            115                 120                 125

Gly Tyr Ile Ser Gly Thr Ala Cys Leu Thr Val Tyr Val Gln Pro Ile
            130                 135                 140

```
Val Ser Leu His Tyr Lys Phe Ser Glu Asp His Leu Asn Ile Thr Cys
145                 150                 155                 160

Ser Ala Thr Ala Arg Pro Ala Pro Met Val Phe Trp Lys Val Pro Arg
                165                 170                 175

Ser Gly Ile Glu Asn Ser Thr Val Thr Leu Ser His Pro Asn Gly Thr
            180                 185                 190

Thr Ser Val Thr Ser Ile Leu His Ile Lys Asp Pro Lys Asn Gln Val
        195                 200                 205

Gly Lys Glu Val Ile Cys Gln Val Leu His Leu Gly Thr Val Thr Asp
    210                 215                 220

Phe Lys Gln Thr Val Asn Lys Gly Gly Gly Ser Gly Gly Gly Gly
225                 230                 235                 240

Ser Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470

<210> SEQ ID NO 7
<211> LENGTH: 473
<212> TYPE: PRT
<213> ORGANISM: Artificial
<220> FEATURE:
<223> OTHER INFORMATION: Synthesized

<400> SEQUENCE: 7

Met Glu Arg Leu Val Ile Arg Met Pro Phe Ser His Leu Ser Thr Tyr
1               5                   10                  15

Ser Leu Val Trp Val Met Ala Ala Val Val Leu Cys Thr Ala Gln Val
            20                  25                  30
```

-continued

```
Gln Val Val Thr Gln Asp Glu Arg Glu Gln Leu Tyr Thr Pro Ala Ser
            35                  40                  45

Leu Lys Cys Ser Leu Gln Asn Ala Gln Glu Ala Leu Ile Val Thr Trp
 50                  55                  60

Gln Lys Lys Lys Ala Val Ser Pro Glu Asn Met Val Thr Phe Ser Glu
 65                  70                  75                  80

Asn His Gly Val Val Ile Gln Pro Ala Tyr Lys Asp Lys Ile Asn Ile
                     85                  90                  95

Thr Gln Leu Gly Leu Gln Asn Ser Thr Ile Thr Phe Trp Asn Ile Thr
                100                 105                 110

Leu Glu Asp Glu Gly Cys Tyr Met Cys Leu Phe Asn Thr Phe Gly Phe
            115                 120                 125

Gly Lys Tyr Ser Gly Thr Ala Cys Leu Thr Val Tyr Val Gln Pro Ile
            130                 135                 140

Val Ser Leu His Tyr Lys Phe Ser Glu Asp His Leu Asn Ile Thr Cys
145                 150                 155                 160

Ser Ala Thr Ala Arg Pro Ala Pro Met Val Phe Trp Lys Val Pro Arg
                165                 170                 175

Ser Gly Ile Glu Asn Ser Thr Val Thr Leu Ser His Pro Asn Gly Thr
                180                 185                 190

Thr Ser Val Thr Ser Ile Leu His Ile Lys Asp Pro Lys Asn Gln Val
            195                 200                 205

Gly Lys Glu Val Ile Cys Gln Val Leu His Leu Gly Thr Val Thr Asp
            210                 215                 220

Phe Lys Gln Thr Val Asn Lys Gly Gly Gly Ser Gly Gly Gly Gly
225                 230                 235                 240

Ser Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
            275                 280                 285

Val Val Asp Val Ser His Glu Asp Pro Glu Val Lys Phe Asn Trp Tyr
            290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
            355                 360                 365

Pro Arg Glu Pro Gln Val Tyr Thr Leu Pro Pro Ser Arg Asp Glu Leu
            370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
                420                 425                 430

Tyr Ser Lys Leu Thr Val Asp Lys Ser Arg Trp Gln Gln Gly Asn Val
            435                 440                 445

Phe Ser Cys Ser Val Met His Glu Ala Leu His Asn His Tyr Thr Gln
```

```
                    450                 455                 460
Lys Ser Leu Ser Leu Ser Pro Gly Lys
465                 470
```

<210> SEQ ID NO 8
<211> LENGTH: 473
<212> TYPE: PRT
<213> ORGANISM: Artificial
<220> FEATURE:
<223> OTHER INFORMATION: Synthesized

<400> SEQUENCE: 8

```
Met Glu Arg Leu Val Ile Arg Met Pro Phe Ser His Leu Ser Thr Tyr
1               5                   10                  15

Ser Leu Val Trp Val Met Ala Ala Val Val Leu Cys Thr Ala Gln Val
            20                  25                  30

Gln Val Val Thr Gln Asp Glu Arg Glu Gln Leu Tyr Thr Pro Ala Ser
        35                  40                  45

Leu Lys Cys Ser Leu Gln Asn Ala Gln Glu Ala Leu Ile Val Thr Trp
    50                  55                  60

Gln Lys Lys Lys Ala Val Ser Pro Glu Asn Met Val Thr Phe Ser Glu
65                  70                  75                  80

Asn His Gly Val Val Ile Gln Pro Ala Tyr Lys Asp Lys Ile Asn Ile
                85                  90                  95

Thr Gln Leu Gly Leu Gln Asn Ser Thr Ile Thr Phe Trp Asn Ile Thr
            100                 105                 110

Leu Glu Asp Glu Gly Cys Tyr Met Cys Leu Phe Asn Thr Phe Gly Phe
        115                 120                 125

Ile Lys Ile Ser Gly Thr Ala Cys Leu Thr Val Tyr Val Gln Pro Ile
    130                 135                 140

Val Ser Leu His Tyr Lys Phe Ser Glu Asp His Leu Asn Ile Thr Cys
145                 150                 155                 160

Ser Ala Thr Ala Arg Pro Ala Pro Met Val Phe Trp Lys Val Pro Arg
                165                 170                 175

Ser Gly Ile Glu Asn Ser Thr Val Thr Leu Ser His Pro Asn Gly Thr
            180                 185                 190

Thr Ser Val Thr Ser Ile Leu His Ile Lys Asp Pro Lys Asn Gln Val
        195                 200                 205

Gly Lys Glu Val Ile Cys Gln Val Leu His Leu Gly Thr Val Thr Asp
    210                 215                 220

Phe Lys Gln Thr Val Asn Lys Gly Gly Gly Ser Gly Gly Gly Gly
225                 230                 235                 240

Ser Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
```

```
                    340                 345                 350
Ala Leu Pro Ala Pro Ile Glu Lys Thr Ile Ser Lys Ala Lys Gly Gln
            355                 360                 365

Pro Arg Glu Pro Gln Val Tyr Thr Leu Pro Pro Ser Arg Asp Glu Leu
        370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470

<210> SEQ ID NO 9
<211> LENGTH: 473
<212> TYPE: PRT
<213> ORGANISM: Artificial
<220> FEATURE:
<223> OTHER INFORMATION: Synthesized

<400> SEQUENCE: 9

Met Glu Arg Leu Val Ile Arg Met Pro Phe Ser His Leu Ser Thr Tyr
1               5                   10                  15

Ser Leu Val Trp Val Met Ala Ala Val Val Leu Cys Thr Ala Gln Val
                20                  25                  30

Gln Val Val Thr Gln Asp Glu Arg Glu Gln Leu Tyr Thr Pro Ala Ser
            35                  40                  45

Leu Lys Cys Ser Leu Gln Asn Ala Gln Glu Ala Leu Ile Val Thr Trp
        50                  55                  60

Gln Lys Lys Lys Ala Val Ser Pro Glu Asn Met Val Thr Phe Ser Glu
65                  70                  75                  80

Asn His Gly Val Val Ile Gln Pro Ala Tyr Lys Asp Lys Ile Asn Ile
                85                  90                  95

Thr Gln Leu Gly Leu Gln Asn Ser Thr Ile Thr Phe Trp Asn Ile Thr
            100                 105                 110

Leu Glu Asp Glu Gly Cys Tyr Met Cys Leu Phe Asn Thr Phe Gly Arg
        115                 120                 125

Gly Lys Ile Ser Gly Thr Ala Cys Leu Thr Val Tyr Val Gln Pro Ile
    130                 135                 140

Val Ser Leu His Tyr Lys Phe Ser Glu Asp His Leu Asn Ile Thr Cys
145                 150                 155                 160

Ser Ala Thr Ala Arg Pro Ala Pro Met Val Phe Trp Lys Val Pro Arg
                165                 170                 175

Ser Gly Ile Glu Asn Ser Thr Val Thr Leu Ser His Pro Asn Gly Thr
            180                 185                 190

Thr Ser Val Thr Ser Ile Leu His Ile Lys Asp Pro Lys Asn Gln Val
        195                 200                 205

Gly Lys Glu Val Ile Cys Gln Val Leu His Leu Gly Thr Val Thr Asp
    210                 215                 220

Phe Lys Gln Thr Val Asn Lys Gly Gly Gly Gly Ser Gly Gly Gly Gly
```

```
                225                 230                 235                 240
Ser Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
            275                 280                 285

Val Val Asp Val Ser His Glu Asp Pro Glu Val Lys Phe Asn Trp Tyr
        290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
            355                 360                 365

Pro Arg Glu Pro Gln Val Tyr Thr Leu Pro Pro Ser Arg Asp Glu Leu
        370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
            435                 440                 445

Phe Ser Cys Ser Val Met His Glu Ala Leu His Asn His Tyr Thr Gln
        450                 455                 460

Lys Ser Leu Ser Leu Ser Pro Gly Lys
465                 470

<210> SEQ ID NO 10
<211> LENGTH: 473
<212> TYPE: PRT
<213> ORGANISM: Artificial
<220> FEATURE:
<223> OTHER INFORMATION: Synthesized

<400> SEQUENCE: 10

Met Glu Arg Leu Val Ile Arg Met Pro Phe Ser His Leu Ser Thr Tyr
1               5                   10                  15

Ser Leu Val Trp Val Met Ala Ala Val Val Leu Cys Thr Ala Gln Val
            20                  25                  30

Gln Val Val Thr Gln Asp Glu Arg Glu Gln Leu Tyr Thr Pro Ala Ser
        35                  40                  45

Leu Lys Cys Ser Leu Gln Asn Ala Gln Glu Ala Leu Ile Val Thr Trp
    50                  55                  60

Gln Lys Lys Lys Ala Val Ser Pro Glu Asn Met Val Thr Phe Ser Glu
65                  70                  75                  80

Lys His Gly Val Val Ile Gln Pro Ala Tyr Lys Asp Lys Ile Asn Ile
                85                  90                  95

Thr Gln Leu Gly Leu Gln Asn Ser Thr Ile Thr Phe Trp Asn Ile Thr
            100                 105                 110

Leu Glu Asp Glu Gly Cys Tyr Met Cys Leu Phe Asn Thr Phe Gly Phe
```

-continued

```
            115                 120                 125
Gly Lys Ile Ser Gly Thr Ala Cys Leu Thr Val Tyr Val Gln Pro Ile
            130                 135                 140

Val Ser Leu His Tyr Lys Phe Ser Glu Asp His Leu Asn Ile Thr Cys
145                 150                 155                 160

Ser Ala Thr Ala Arg Pro Ala Pro Met Val Phe Trp Lys Val Pro Arg
                165                 170                 175

Ser Gly Ile Glu Asn Ser Thr Val Thr Leu Ser His Pro Asn Gly Thr
                180                 185                 190

Thr Ser Val Thr Ser Ile Leu His Ile Lys Asp Pro Lys Asn Gln Val
                195                 200                 205

Gly Lys Glu Val Ile Cys Gln Val Leu His Leu Gly Thr Val Thr Asp
            210                 215                 220

Phe Lys Gln Thr Val Asn Lys Gly Gly Gly Ser Gly Gly Gly Gly
225                 230                 235                 240

Ser Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
                260                 265                 270

Pro Lys Asp Thr Leu Met Ile Ser Arg Thr Pro Glu Val Thr Cys Val
                275                 280                 285

Val Val Asp Val Ser His Glu Asp Pro Glu Val Lys Phe Asn Trp Tyr
290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
                340                 345                 350

Ala Leu Pro Ala Pro Ile Glu Lys Thr Ile Ser Lys Ala Lys Gly Gln
                355                 360                 365

Pro Arg Glu Pro Gln Val Tyr Thr Leu Pro Pro Ser Arg Asp Glu Leu
                370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
                420                 425                 430

Tyr Ser Lys Leu Thr Val Asp Lys Ser Arg Trp Gln Gln Gly Asn Val
                435                 440                 445

Phe Ser Cys Ser Val Met His Glu Ala Leu His Asn His Tyr Thr Gln
                450                 455                 460

Lys Ser Leu Ser Leu Ser Pro Gly Lys
465                 470
```

<210> SEQ ID NO 11
<211> LENGTH: 10
<212> TYPE: PRT
<213> ORGANISM: Artificial
<220> FEATURE:
<223> OTHER INFORMATION: Synthesized

<400> SEQUENCE: 11

Gly Gly Gly Gly Ser Gly Gly Gly Gly Ser

<210> SEQ ID NO 12
<211> LENGTH: 278
<212> TYPE: PRT
<213> ORGANISM: Artificial
<220> FEATURE:
<223> OTHER INFORMATION: Synthesized

<400> SEQUENCE: 12

| | | | | | | | | | | | | | | | |
|---|---|---|---|---|---|---|---|---|---|---|---|---|---|---|---|
| Met | Glu | Arg | Leu | Val | Ile | Arg | Met | Pro | Phe | Ser | His | Leu | Ser | Thr | Tyr |
| 1 | | | | 5 | | | | | 10 | | | | | 15 | |
| Ser | Leu | Val | Trp | Val | Met | Ala | Ala | Val | Val | Leu | Cys | Thr | Ala | Gln | Val |
| | | | 20 | | | | | 25 | | | | | 30 | | |
| Gln | Val | Val | Thr | Gln | Asp | Glu | Arg | Glu | Gln | Leu | Tyr | Thr | Pro | Ala | Ser |
| | | | | 35 | | | | | 40 | | | | | 45 | |
| Leu | Lys | Cys | Ser | Leu | Gln | Asn | Ala | Gln | Glu | Ala | Leu | Ile | Val | Thr | Trp |
| | 50 | | | | | 55 | | | | | 60 | | | | |
| Gln | Lys | Lys | Lys | Ala | Val | Ser | Pro | Glu | Asn | Met | Val | Thr | Phe | Ser | Glu |
| 65 | | | | | 70 | | | | | 75 | | | | | 80 |
| Asn | His | Gly | Val | Val | Ile | Gln | Pro | Ala | Tyr | Lys | Asp | Lys | Ile | Asn | Ile |
| | | | | 85 | | | | | 90 | | | | | 95 | |
| Thr | Gln | Leu | Gly | Leu | Gln | Asn | Ser | Thr | Ile | Thr | Phe | Trp | Asn | Ile | Thr |
| | | | 100 | | | | | 105 | | | | | 110 | | |
| Leu | Glu | Asp | Glu | Gly | Cys | Tyr | Met | Cys | Leu | Phe | Asn | Thr | Phe | Gly | Phe |
| | | | | 115 | | | | | 120 | | | | | 125 | |
| Gly | Tyr | Ile | Ser | Gly | Thr | Ala | Cys | Leu | Thr | Val | Tyr | Val | Gln | Pro | Ile |
| | 130 | | | | | 135 | | | | | 140 | | | | |
| Val | Ser | Leu | His | Tyr | Lys | Phe | Ser | Glu | Asp | His | Leu | Asn | Ile | Thr | Cys |
| 145 | | | | | 150 | | | | | 155 | | | | | 160 |
| Ser | Ala | Thr | Ala | Arg | Pro | Ala | Pro | Met | Val | Phe | Trp | Lys | Val | Pro | Arg |
| | | | | 165 | | | | | 170 | | | | | 175 | |
| Ser | Gly | Ile | Glu | Asn | Ser | Thr | Val | Thr | Leu | Ser | His | Pro | Asn | Gly | Thr |
| | | | 180 | | | | | 185 | | | | | 190 | | |
| Thr | Ser | Val | Thr | Ser | Ile | Leu | His | Ile | Lys | Asp | Pro | Lys | Asn | Gln | Val |
| | | | | 195 | | | | | 200 | | | | | 205 | |
| Gly | Lys | Glu | Val | Ile | Cys | Gln | Val | Leu | His | Leu | Gly | Thr | Val | Thr | Asp |
| | 210 | | | | | 215 | | | | | 220 | | | | |
| Phe | Lys | Gln | Thr | Val | Asn | Lys | Gly | Tyr | Trp | Phe | Ser | Val | Pro | Leu | Leu |
| 225 | | | | | 230 | | | | | 235 | | | | | 240 |
| Leu | Ser | Ile | Val | Ser | Leu | Val | Ile | Leu | Leu | Val | Leu | Ile | Ser | Ile | Leu |
| | | | | 245 | | | | | 250 | | | | | 255 | |
| Leu | Tyr | Trp | Lys | Arg | His | Arg | Asn | Gln | Asp | Arg | Gly | Glu | Leu | Ser | Gln |
| | | | 260 | | | | | 265 | | | | | 270 | | |
| Gly | Val | Gln | Lys | Met | Thr | | | | | | | | | | |
| | | | 275 | | | | | | | | | | | | |

<210> SEQ ID NO 13
<211> LENGTH: 278
<212> TYPE: PRT
<213> ORGANISM: Artificial
<220> FEATURE:
<223> OTHER INFORMATION: Synthesized

<400> SEQUENCE: 13

| | | | | | | | | | | | | | | | |
|---|---|---|---|---|---|---|---|---|---|---|---|---|---|---|---|
| Met | Glu | Arg | Leu | Val | Ile | Arg | Met | Pro | Phe | Ser | His | Leu | Ser | Thr | Tyr |
| 1 | | | | 5 | | | | | 10 | | | | | 15 | |

```
Ser Leu Val Trp Val Met Ala Ala Val Val Leu Cys Thr Ala Gln Val
             20              25                  30
Gln Val Val Thr Gln Asp Glu Arg Glu Gln Leu Tyr Thr Pro Ala Ser
         35              40                  45
Leu Lys Cys Ser Leu Gln Asn Ala Gln Glu Ala Leu Ile Val Thr Trp
     50              55                  60
Gln Lys Lys Lys Ala Val Ser Pro Glu Asn Met Val Thr Phe Ser Glu
65              70                  75                      80
Asn His Gly Val Val Ile Gln Pro Ala Tyr Lys Asp Lys Ile Asn Ile
                 85                  90                  95
Thr Gln Leu Gly Leu Gln Asn Ser Thr Ile Thr Phe Trp Asn Ile Thr
             100                 105                 110
Leu Glu Asp Glu Gly Cys Tyr Met Cys Leu Phe Asn Thr Phe Gly Phe
         115                 120                 125
Gly Lys Tyr Ser Gly Thr Ala Cys Leu Thr Val Tyr Val Gln Pro Ile
     130                 135                 140
Val Ser Leu His Tyr Lys Phe Ser Glu Asp His Leu Asn Ile Thr Cys
145                 150                 155                 160
Ser Ala Thr Ala Arg Pro Ala Pro Met Val Phe Trp Lys Val Pro Arg
                 165                 170                 175
Ser Gly Ile Glu Asn Ser Thr Val Thr Leu Ser His Pro Asn Gly Thr
             180                 185                 190
Thr Ser Val Thr Ser Ile Leu His Ile Lys Asp Pro Lys Asn Gln Val
         195                 200                 205
Gly Lys Glu Val Ile Cys Gln Val Leu His Leu Gly Thr Val Thr Asp
     210                 215                 220
Phe Lys Gln Thr Val Asn Lys Gly Tyr Trp Phe Ser Val Pro Leu Leu
225                 230                 235                 240
Leu Ser Ile Val Ser Leu Val Ile Leu Leu Val Leu Ile Ser Ile Leu
                 245                 250                 255
Leu Tyr Trp Lys Arg His Arg Asn Gln Asp Arg Gly Glu Leu Ser Gln
             260                 265                 270
Gly Val Gln Lys Met Thr
             275
```